United States Patent [19]

Naito et al.

[11] 4,446,318

[45] May 1, 1984

[54] METHOD FOR PRODUCING 7-AMINOCEPHEM COMPOUNDS

[75] Inventors: Kenzo Naito, Kyoto; Haruo Shinbo, Nishinomiya; Kazuo Tsukamura, Hyogo, all of Japan

[73] Assignee: Takeda Chemical Industries, Ltd., Osaka, Japan

[21] Appl. No.: 318,960

[22] Filed: Nov. 6, 1981

[30] Foreign Application Priority Data

Nov. 11, 1980 [JP] Japan .................. 55-159208
Jun. 17, 1981 [JP] Japan .................. 56-93293

[51] Int. Cl.$^3$ ............... C07D 501/04; C07D 501/02
[52] U.S. Cl. ...................................... 544/26; 544/16; 544/21; 544/30
[58] Field of Search ................ 544/26, 27, 16, 28, 544/21; 424/246

[56] References Cited

U.S. PATENT DOCUMENTS 4,312,986  1/1982  Saikawa et al. ............... 544/27
4,317,907  3/1982  Saikawa et al. ............... 544/21

Primary Examiner—Nicholas S. Rizzo
Attorney, Agent, or Firm—Wegner & Bretschneider

[57] ABSTRACT

An improvement, in per se known method for producing 7-aminocephem compound being important intermediate for producing antimicrobial substances, represented by the formula:

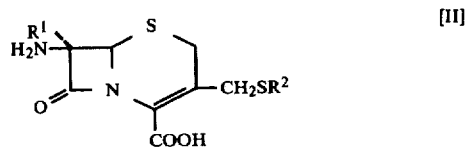

wherein $R^1$ is a hydrogen atom or a methoxy group and $R^2$ is a residue of a thiol compound, or a salt or ester thereof, by reacting a compound of the formula:

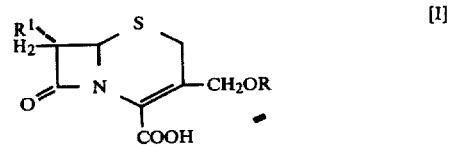

wherein $R^1$ is as defined above and R is a carboxylic acid acyl group, or a salt or ester thereof, with a thiol compound or a salt thereof, is characterized in that the reaction is conducted in an organic solvent in the presence of a dihalophosphoric acid to give the compound [II] in high yield and high purity.

12 Claims, No Drawings

METHOD FOR PRODUCING 7-AMINOCEPHEM COMPOUNDS

The present invention relates to an improvement in the method for producing 7-aminocephem compounds of the formula:

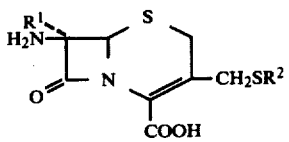

[II]

wherein $R^1$ is a hydrogen atom or a methoxy group and $R^2$ is a residue of a thiol compound, or salts or esters thereof, which comprises reacting a compound of the formula:

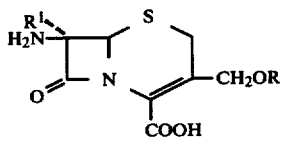

[I]

wherein $R^1$ is as defined above and R is a carboxylic acid acyl group, or a salt or ester thereof with a thiol compound or a salt thereof.

The compounds of the formula [I] are those which are easily produced on an industrial scale from fermentation products such as cephalosporin C or deacetylcephalosporin C, and the compounds of the formula [II] are important intermediates for producing antimicrobial substances. Therefore, the process, which enables [II] to be produced in improved yields by way of industrially advantageous procedures with the use of [I] as starting materials, is required, and there have been so far known ① a procedure comprising reaction of [I] with a thiol compound in water or a mixed solvent of water and organic solvent(s) under acid to weakly basic conditions (e.g. Japanese Published Examined Patent Application Nos. 17936/1964 and 13023/1971, U.S. Pat. No. 3,641,021, B.P. No. 1283811 and No. 1321412, and OLS No. 2262477, etc.), ② a procedure comprising heating [I] and a thiol compound in organic solvent(s) (e.g. Japanese Published Unexamined Patent Application No. 43043/1980, etc.), ③ a procedure comprising reaction of [I] with a thiol compound in organic solvent(s) in the presence of an acid or acid adduct (e.g. OLS No. 2804896, B.P. No. 1565941, No. 2027429 and No. 2048257, Japanese Published Unexamined Patent Application Nos. 20724/1980, 49383/1980 and 153790/1980, etc.), and the like. However, the procedures ① and ② deteriorate the product quality and give a poor yield of the objective compound due to occurrence of the β-lactam hydrolysis and the like under the reaction conditions, and the procedure ③ encounters the problems in that there are liable to occur undesirable side reactions such as conversion to lactone or opening of the β-lactam ring of [I] and/or [II], that utilization of a Lewis acid or an adduct thereof as acid limits the type of reaction equipment and brings about difficulties in the post-treatment step, that after the conclusion of the reaction, the used acid is required to be neutralized for isolation with an alkali which, in contact with the objective compound, tends to cause decomposition and coloration, and that the yield of the objective compound [II] becomes extremely worse, depending upon the types of the starting materials [I] and acids, and others. Occurrence of the conversion to lactone, decomposition of the β-lactam and coloration causes impurities derived therefrom to get mixed in the objective compound [II], which contributes to much time and labor required in the removal of such impurities as well as lowered yields, when such objective compound [II] is led to antimicrobial substances. In the procedure ③, furthermore, there arises the need to lower the water and/or moisture content of the starting materials [I] in order to avoid contamination with water and/or moisture in the reaction system, and this presents disadvantages to industrialization of the procedure in that the drying step is required to be added and that dried powder is easy to be scattered and therefore deteriorates the working environment, as is reflected for example in the property of 7-aminocephalosporanic acid to cause contact dermatitis to man, etc. (Kirk-Othmer, Encyclopedia of Chemical Technology, 3rd edition, 1978, volume 2, p. 907 to 908). On the other hand, the compounds [I], as normally produced by the precipitation at isoelectric point from water or mixed solvents of water and organic solvents, contain water and/or moisture, and wet materials containing water and/or moisture are harder to be scattered than dried powder. In addition, it has been confirmed that the procedure ③, in cases in which 3-substituents of the starting materials [I] are those susceptible to enolization, brings about side reactions such as the conversion to lactone, resulting in lowered yields and enhanced contamination of the objective compounds with the lactone form.

The present inventors, after having conducted extensive investigation with a specific view to solving these problems, found that the reaction of a compound [I] or a salt or ester thereof with a thiol or a salt thereof in an organic solvent in the presence of a dihalophosphoric acid

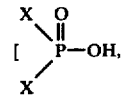

wherein X is chlorine, bromine or fluorine], unexpectedly, affords the objective compound [II] in an improved yield and that the above-mentioned problems can be solved, and, on the basis of such findings, have completed the present invention.

Thus, the present invention relates to an improvement in per se known reaction of a compound [I] or a salt or ester thereof with a thiol compound or a salt thereof, characterized in that said reaction is conducted in an organic solvent in the presence of a dihalophosphoric acid.

In the compounds having the formula [I] which are used as the starting materials in the present invention, the carboxylic acid acyl groups represented by R, which are operable, include alkanoyl groups (preferably $C_{1-4}$) such as acetyl, propionyl and butyryl; alkenoyl groups (preferably $C_{2-6}$) such as acryl; aroyl groups (preferably $C_{7-9}$) such as benzoyl; aralkanoyl groups (preferably $C_{8-12}$) such as phenylacetyl; carbamoyl group, etc., and these acyl groups may be further substituted, whereby as such substituent, for example, use is made of halogen atoms, nitro group, oxo group, alkyl group, alkoxy group, alkylthio group, acyl group, acyloxy group, acylamino group, hydroxyl group, carboxyl group, carbonyl group, sulfamoyl group, carbamoyl group, carboalkoxycarbamoyl group, aroylcarbamoyl group, carboalkoxysulfamoyl group, sulfonyl group, and the like. Among others, frequent use is made of, for example, $C_{1-4}$ alkanoyl which may be substituted with oxo (e.g. acetyl, 3-oxobutyryl groups), etc.

As the 4-esterified derivatives of the compounds of the formulas [I] and [II] in the present invention, use is made of esters in the carboxyl group at the 4-position such as alkyl esters, cycloalkyl esters and cycloalkenyl esters, which do not affect adversely the reaction, having or not having substituents, e.g. methyl, ethyl, propyl, isopropyl, butyl, t-butyl, methoxymethyl, ethoxymethyl, isopropoxymethyl, α-methoxyethyl, α-ethoxyethyl, phenoxymethyl, dimethylaminoethyl, diethylaminoethyl, phenacyl, acetylmethyl, p-bromophenacyl, acetoxymethyl, 1-(ethoxycarbonyloxy)ethyl, pivaloyloxymethyl, α-acetoxybutyl, benzoyloxymethyl, 1,1-diacetylalkylmethanesulfonylethyl, toluenesulfonylethyl, trichloroethyl, (1,3-dioxol-5-methyl-2-one-4-yl)methyl, cyanomethyl and phthalimidomethyl. The compounds of the formulas [I] and [II] or their 4-esterified derivatives include salts in the acidic groups in the molecule or salts in the basic groups. As the salts in the acidic groups, use is made of salts with alkali metals such as sodium and potassium; salts with alkaline earth metals such as calcium and magnesium and salts with nitrogen-containing organic bases such as triethylamine, N-methylpiperidine, dicyclohexylamine and tributylamine, while as the salts in the basic groups, use is made of salts with mineral acids such as hydrochloric acid and sulfuric acid and salts with organic acids such as fatty acids, e.g. formic acid and trifluoroacetic acid, and sulfonic acids, e.g. methanesulfonic acid and toluenesulfonic acid. As the group $R^1$, use is made of hydrogen and methoxy group.

Further, $R^2$ in the formula [II] represents a residue of a thiol compound ($R^2SH$), which is specifically exemplified by alkyl groups (preferably $C_{1-6}$) such as methyl, ethyl, propyl and butyl; cycloalkyl groups (preferably $C_{3-8}$) such as cyclohexyl and cyclobutyl; aryl groups (preferably $C_{6-12}$) such as phenyl and naphthyl; aralkyl groups (preferably $C_{7-12}$) such as benzyl; acyl groups (preferably $C_{2-6}$) such as acetyl; alkoxythiocarbonyl groups (preferably $C_{2-8}$) such as methoxythiocarbonyl; and heterocyclic groups including, for example, 5 to 8-membered heterocyclic rings having one to a few number of hetero-atoms such as nitrogen (inclusive of N-oxide), oxygen and sulfur, as well as fused rings corresponding thereto, such as oxazolyl, thiazolyl, isoxazolyl, isothiazolyl, imidazolyl, pyrazolyl, pyridyl, N-oxypyridyl, pyrazyl, pyrimidinyl, pyridazinyl, N-oxypyridazinyl, quinolyl, isoquinolyl, quinazolyl, indolyl, indazolyl, oxadiazolyl, thiadiazolyl, triazolyl, thiatriazolyl, tetrazolyl, triazinyl, benzimidazolyl, benzoxazolyl, benzothiazolyl, triazolopyridyl and pyridine-1-oxido-2-yl, pyrido-[2,3-d]pyrimidyl, benzopyranyl, 1,8-, 1,5-, 1,6-, 1,7-, 2,7- or 2,6-naphthyridyl, thieno[2,3-b]-pyridyl and the like. These may be further substituted by halogen atoms (e.g. Cl, Br, I, etc.), alkyl, aryl, hydroxyl, alkoxy (e.g. methoxy, ethoxy, propoxy, etc.), alkylthio, nitro, cyano, oxy, amino, alkylamino, dialkylamino, acylamino, acyl, acyloxy, carboxyl, sulfo, carbamoyl, aminoalkyl, N-alkylaminoalkyl, N,N-dialkylaminoalkyl, hydroxyalkyl, carboxyalkyl, sulfoalkyl, sulfamoylalkyl, sulfamoyl and carbamoylalkyl groups, etc. (wherein alkyl, aryl and acyl groups include, for example, those exemplified above), whereby hydroxyl, amino and carboxyl groups, etc. out of these substituents may be protected by protective groups normally employed. As the protective group for amino which may optionally be protected, any of those used for this purpose in the field of β-lactam or peptide synthesis may conveniently be employed. Examples of such amino-protecting group include aromatic acyl groups such as phthaloyl, p-nitrobenzoyl, p-tert-butylbenzoyl, p-tert-butylbenzenesulfonyl, benzenesulfonyl, toluenesulfonyl, etc., aliphatic acyl groups such as formyl, acetyl, propionyl, monochloroacetyl, dichloroacetyl, trichloroacetyl, methanesulfonyl, ethanesulfonyl, trifluoroacetyl, maleyl, succinyl, etc., and esterified carboxyl groups such as methoxycarbonyl, ethoxycarbonyl, t-butoxycarbonyl, isopropoxycarbonyl, 2-cyanoethoxycarbonyl, trichloroethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl, phenyloxycarbonyl, etc., as well as nonacyl amino-protecting groups such as trityl, 2-nitrophenylthio, benzylidene, 4-nitrobenzylidine, trialkylsilyl, benzyl, p-nitrobenzyl, etc. The choice of amino-protecting group is not critical in the present invention. The protective group for carboxyl includes any group which can be conventionally used as a carboxy-protecting group in the fields of β-lactam and other organic chemistry, such as ester residues (e.g., methyl, ethyl, n-propyl, isopropyl, tert-butyl, tert-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-tert-butyl-4-hydroxybenzyl, mesylmethyl, benzenesulfonylmethyl, phenylthiomethyl, dimethylaminoethyl, pyridine-1-oxido-2-methyl, methylsulfinylmethyl, bis(p-methoxyphenyl)-methyl, 2-cyano-1,1-dimethylethyl, etc.), silyl, and the like. The protective group for hydroxyl includes any group which can be conventionally used as a hydroxy-protecting group in the fields of β-lactam and other organic chemistry, such as ether residues, e.g. tert-butyl, benzyl, p-nitrobenzyl, trityl, methylthiomethyl, β-methoxyethoxymethyl, etc.; silylether residues, e.g., trimethylsilyl, tertbutyldimethylsilyl, etc.; acetal residues, e.g., 2-tetrahydropyranyl, 4-methoxy-4-tetrahydropyranyl, etc. and the like. The choice of the above-mentioned hydroxy-protecting group is not critical in the present invention, as is the case with the amino- and carboxy-protecting groups.

The heterocyclic group for $R^2$ is preferably a group of the formula

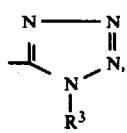

the formula the formula

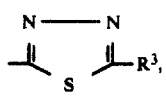

the formula

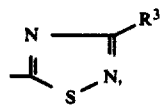

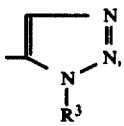

or the formula

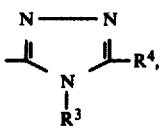

where $R^3$ is hydrogen, a lower alkyl group of 1 to 3 carbon atoms (e.g. methyl), a hydroxy-substituted lower alkyl group (e.g. 2-hydroxyethyl), a carboxyalkyl group (e.g. carboxymethyl), or a di-lower alkyl-substituted aminoalkyl group (e.g. 2-dimethylaminoethyl); $R^4$ is a lower alkyl group (e.g. methyl) or a hydroxy-substituted lower alkyl group (e.g. hydroxymethyl). Especially, when $R^2$ is 1-(di-loweralkyl-substituted)aminoalkyl-1H-tetrazolyl, a desirable result is obtained.

Also, the thiols used in the present invention can take the form of either basic or acidic salt, depending upon the kind of $R^2$, and any of such basic and acidic salts are included in the starting material of the present invention. As such salts, use is made of the salts in the basic and acidic groups as mentioned with reference to the aforementioned formulas [I] and [II].

In the process of the present invention, the 7-aminocephem compounds [II] or their salts or esters are obtained by reacting the compound [I] or its salt or ester with a thiol compound or its salt in an organic solvent in the presence of a dihalophosphoric acid.

The compound [I] or its salt or ester, a thiol compound or its salt, a dihalophosphoric acid and an organic solvent may be mixed in any order, but normally, the process is carried out by mixing the compound [I] or its salt or ester with a thiol compound or its salt in an organic solvent and then adding a dihalophosphoric acid, by mixing a thiol compound or its salt with an organic solvent and then adding a dihalophosphoric acid and next the compound [I] or its salt or ester, or by mixing a dihalophosphoric acid with an organic solvent and then adding a thiol compound or its salt and next the compound [I] or its salt or ester. In any of the above mixing procedures, it is advantageous to carry out the mixing step of a dihalophosphoric acid under cooling (for example, at $-40°$ to $30°$ C.).

As the solvent which is useful in the reaction, use may be made of any organic solvents which do not affect adversely the reaction. Such solvents include preferably nitriles such as acetonitrile, propionitrile and malonodinitrile; nitroalkanes such as nitromethane, nitroethane, and nitropropane, aromatic hydrocarbons such as benzene, toluene, xylene, nitrobenzene and fluorobenzene; esters such as methyl acetate, ethyl acetate and ethylene carbonate; halogenated hydrocarbons such as methylene chloride, 1,2-dichloroethane and 1,1,1-trichloroethane; organic carboxylic acids such as acetic acid and propionic acid; ethers such as diethyl ether, dioxane, tetrahydrofuran and ethylene glycol dimethyl ether; sulfolanes such as sulfolane, and the like, and these solvents can be used in mixtures of more than two kinds. Among others, frequent use is made of, for example, nitriles (e.g. acetonitrile), nitroalkanes (e.g. nitromethane), esters (e.g. ethyl acetate), halogenated hydrocarbons (e.g. methylene chloride), etc. The amount of such solvents to be used is normally 0.1 to 10.0 l, preferably 0.5 to 7.0 l per 1 mole of the starting material [I].

The amount of a thiol compound or its salt to be used in the reaction may be equimolar against the compound [I] or its salt or ester, but in some instances, is desirably useful in the range of 1.0–3.0 moles per 1 mole of the latter. The optimal amount of a dihalophosphoric acid to be used varies depending upon types of the starting material of the compound [I] and thiol compounds, kind of solvents to be used, etc., and normally is 4 to 24 moles per 1 mole of the compound of the formula [I]. Specifically, it is advantageous to use, against 1 mole of the compound [I] ($R^1$=H, R=COCH$_3$ or COCH$_2$COCH$_3$), 1.0 to 1.5 moles of a thiol compound $$\underset{CH_2CH_2N(CH_3)_2}{(HS\!-\!\underset{N}{\underset{|}{\overset{N\!-\!-\!-\!N}{\|\,\,\,\,\,\|}}}\!\!N\!-\!N)},$$

8.0 to 12.0, preferably 9.0–10.0 moles (R=COCH$_3$) or 10.0 to 14.0, preferably 11.0–12.0 moles (R=COCH$_2$COCH$_3$) of a dihalophosphoric acid and 0.5 to 5.0 l of acetonitrile as a solvent, and in the case of $$\underset{CH_3}{HS\!-\!\underset{N}{\underset{|}{\overset{N\!-\!-\!-\!N}{\|\,\,\,\,\,\|}}}\!\!N\!-\!N}$$

being utilized as a thiol compound, it is preferred to employ 1.0 to 2.0 moles of the thiol compound, 7.0 to 14.0, preferably 8.0–12.0 moles (R=COCH$_3$) or 9.0 to 16.0 preferably 11.0–15.0 moles (R=COCH$_2$COCH$_3$), of a dihalophosphoric acid and 0.5 to 5.0 l of acetonitrile as a solvent. The reaction temperature is desirably not higher than room temperature at the stage of adding a dihalophosphoric acid, and it is normally added at $-40°$ to $10°$ C. When after adding it the reaction is carried out at $0°$ to $70°$ C., there may be produced good results. The reaction time varies depending upon the types and amounts of the starting compound [I], thiol compounds, solvents, etc. to be used as well as the reaction temperature, but is several minutes to several ten hours. The reaction, in which the above mentioned organic solvents are used, can also be carried out, if desired, by adding a dihalophosphoric acid and then distilling off the organic solvent partly or wholly. In addition, it is also possible to obtain the objective 7-aminocephem compounds [II] or their 4-esterified derivatives without the use of any organic solvent by reacting the compound [I] or its 4-esterified derivative with a solution obtained by mixing a thiol compound with a dihalophosphoric acid. When no solvent is used, there result industrial advantages such as reduction of the size of a reaction vessel. As the dihalophosphoric acid, further, use is made of dihalophosphoric acids produced by the procedures, such as the reaction of phosphorus oxyhalide with water (J. Goubeau et al., Z. Physik. Chem., vol. 14, p. 49, 1958);

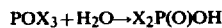

$$POX_3 + H_2O \rightarrow X_2P(O)OH$$

the reaction of diphosphoryl tetrahalide with water (H. Grunze et al., Ang. Chem., vol. 70, p. 73, 1958);

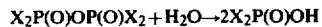

$$X_2P(O)OP(O)X_2 + H_2O \rightarrow 2X_2P(O)OH$$

the reaction of diphosphoryl tetrahalide (pyrophosphoryl tetrahalide) with alcohols (H. Grunze, Chem. Ber., vol. 92, p. 850, 1959);

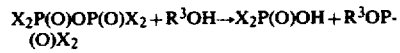

$$X_2P(O)OP(O)X_2 + R^3OH \rightarrow X_2P(O)OH + R^3OP(O)X_2$$

(wherein X is the above mentioned halogen atom; $R^3$ is a residue of an alcohol), the reaction of phosphoric anhydride, water and phosphorus oxyhalide (R. V. Wazer et. al., J. Am. Chem. Soc., vol. 81, p. 6360, 1959);

$$P_4O_{10} + 6H_2O + 8POX_3 \rightarrow 12X_2P(O)OH$$

the reaction of phosphoric anhydride, phosphorus pentahalide and phosphoric acid (the above-mentioned literature by R. V. Wazer, etc.);

$$P_4O_{10} + 6PX_5 + 5H_3PO_4 \rightarrow 15X_2P(O)OH$$

(wherein X is the above-mentioned halogen atom), or the process for producing difluorophosphoric acid, which comprises reacting phosphoric anhydride with anhydrous hydrogen fluoride, followed by the fractional distillation under reduced pressure (L. C. Mosier et.al., Ind. Eng. Chem., vol. 43, p. 246, 1951), or procedures similar thereto. Among others, it is advantageous to use dichlorophosphoric acid. Though the dihalophosphoric acid may be first produced by these procedures and then used in the process of the present invention, the process may also be carried out, for example, by mixing the compound [I] or its 4-esterified derivative with a thiol compound and water in an organic solvent, followed by the addition of diphosphoryl tetrahalide, or by mixing the compound [I] or its 4-esterified derivative with an organic solvent, and adding a starting material for dihalophosphoric acid, followed by the addition of a thiol compound. Furthermore, the compound [I] or its 4-esterified derivative can be mixed with a starting material for dihalophosphoric acid, followed by mixing the resultant mixture with a thiol compound and an organic solvent. Water to be used in the production of a dihalophosphoric acid may be the water and/or moisture contained in the compound of the formula [I] or the water and/or moisture in the wet material of [I], or may be added on the occasion of the reaction, whereby the water and/or moisture contained in the starting material [I] or the total sum of such water and/or moisture and added water may be in the range of 1 to 20 moles per 1 mole of the compound of the formula [I] to be used in the reaction, preferably 2 to 8 moles per 1 mole of the compound [I]. For example, the amount of diphosphoryl tetrachloride to be used in the reaction is nearly equimolar with the total amount of water to be used in the reaction, preferably 0.8 to 1.2 moles per 1 mole of the latter. The used amount of diphosphoryl tetrachloride is set by the amount of water to be used in the reaction. The optimal amount of diphosphoryl tetrachloride to be used varies depending upon types of the starting compound [I] and thiol compounds, kind of solvents to be used, etc., and is normally 2 to 12 moles per 1 mole of the compound of the formula [I]. Specifically, it is advantageous to use, against 1 mole of the compound [I] ($R^1 = H$, $R = COCH_3$ or $COCH_2COCH_3$), 1.0 to 1.5 moles of a thiol compound

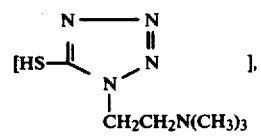

4.0 to 6.0, preferably 4.5–5.0 moles ($R = COCH_3$), or 5.0 to 7.0, preferably 5.5–6.0 moles ($R = COCH_2COCH_3$), each of water and diphosphoryl tetrachloride, and 0.5 to 5.0 l of acetonitrile as a solvent, and in the case of

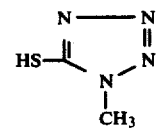

being used as a thiol compound, it is preferred to employ 1.0 to 2.0 moles of the thiol compound, 3.5 to 7.0, preferably 4.0–6.0 moles ($R = COCH_3$), or 4.5 to 8.0, preferably 5.5–7.5 moles ($R = COCH_2COCH_3$), each of water and diphosphoryl tetrachloride, and 0.5 to 5.0 l of acetonitrile as a solvent.

After the conclusion of the reaction, the objective compound [II] can also be obtained in the forms of crystals or powder easy to be filtered as the hydrogen halide salt by the salting out procedure, which, for example, comprises adding to the reaction solution hydrogen halide (e.g. HCl, HBr, etc.) or a solution of hydrogen halide in an organic solvent (e.g. the above-mentioned organic solvents to be used in the present reaction, etc.) and an organic solvent (e.g. the above-mentioned organic solvents to be used in the present reaction, especially, ether, acetonitrile, etc.), or comprises adding to the reaction solution alcohols (e.g. methanol, ethanol, propanol, isopropanol, butanol, isobutanol, etc.) and then adding an organic solvent in which hydrogen halide salts of the compound [II] are sparingly soluble (e.g. the above-mentioned organic solvents to be used in the present reaction, especially, acetonitrile, methylene chloride, ethyl acetate, ether, tetrahydrofuran, etc.) and a small amount of water, if desired, and the like. The process of the present invention, which permits such isolation procedures to be employed, is greatly advantageous in that it can avoid decomposition, coloration, etc. of the objective compound [II] which are encountered by the conventional processes in neutralizing the reaction solution to the isoelectric point with an alkali during isolation of the objective compound [II], that it can easily isolate even an objective compound [II] which, with its strong water-solubility and properties hindering the precipitation at isoelectric point, is difficult to be isolated by conventional procedures, and that it affords the objective compound [II] not containing the water and/or moisture in the form of hydrogen halide salts without complex drying steps required, when the objective compound [II] is necessarily subjected to an acylation reaction under anhydrous conditions in the subsequent step. The compound [II] obtained by the above proceudre, as such or after being subjected to further purification, can be used as starting materials for the production of antimicrobial substances. For example, there can be obtained 7-[2-(2-aminothiazol-4-yl)-acetamido]-3-[1-(2-N,N-dimethylaminoethyl)-1H-tetrazol-5-yl]thiomethyl-3-cephem-4-carboxylic acid and 7-[2-(2-aminothiazol-4-yl)-2-(syn)-methoxyaminoacetamido]-3-(1-methyl-1H-tetrazol-5-yl)thiomethyl-3-cephem-4-carboxylic acid by the reaction of [II] with (2-aminothiazol-4-yl)-acetic acid or its reactive derivative and the reaction of [II] with 2-(2-aminothiazol-4-yl)-2-(syn)-methoxyiminoacetic acid or its reactive derivative, respectively.

The following Examples are intended to illustrate this invention in further detail and should by no means be construed as limiting the scope of the invention.

And, symbols used in Examples and so on have the following meanings, respectively;

| 7-ACA | 7-aminocephalosporanic acid |
|-------|------------------------------|
| DCPA  | dichlorophosphoric acid |
| s     | singlet |
| br-s  | broad singlet |
| d     | doublet |
| dd    | double doublets |
| t     | triplet |
| q     | quartet |
| AB-q  | AB type quartet |
| m     | multiplet |
| sh    | shoulder |
| l     | liter |
| ml    | milliliter |
| g     | gram |
| mg    | milligram |
| kg    | kilogram |

EXAMPLE 1

A 320 ml portion of acetonitrile was added to 54.5 g of 7-ACA and 25,6 g of 5-mercapto-1-methyl-1H-tetrazole, and 296.7 g of DCPA was added to the mixture with stirring and under cooling at $-20°$ to $-10°$ C. After the dissolution, the reaction mixture was stirred at 15° to 17° C. for 40 minutes to allow the reaction to proceed, cooled and poured into 1.8 kg of ice-water. The mixture was allowed to stand at 5° C. overnight, cooled by adding ice under stirring and adjusted to pH 4.0 with 25% aqueous ammonia. The resulting precipitate was recovered by filtration, washed with 480 ml of cold water and 500 ml of acetone successively, and dried, thereby affording 62.2 g (94.7% of yield) of 7-amino-3-(1-methyl-1H-tetrazol-5-yl)thiomethyl-3-cephem-4-carboxylic acid.

IR(KBr): cm$^{-1}$ 3400, 3140, 2990, 2600, 1795, 1617, 1540.

NMR(D$_2$O+CF$_3$COOD)δ: 3.74(2H,s,2—CH$_2$), 4.10(3H,s,N—CH$_3$), 4.37(2H,s,3—CH$_2$), 5.19(1H,d,J=5 Hz,C$_6$—H), 5.32(1H,d,J=5 Hz,C$_7$—H).

Elemental analysis (C$_{10}$H$_{12}$N$_6$S$_2$O$_3$.0.5H$_2$O): Found: C, 35.85; H, 3.86; N, 24.73; Calcd.: C, 35.60; H, 3.88; N, 24.91.

EXAMPLE 2

A 11 ml portion of acetonitrile was added to 2.72 g of 7-ACA and 1.28 g of 5-mercapto-1-methyl-1H-tetrazole, and 14.9 g of DCPA was added through a dropping funnel to the mixture with stirring and under cooling at $-25°$ to $-20°$ C., followed by rinsing the funnel with 1 ml of acetonitrile. The reaction mixture was warmed to 15° C., stirred at 14° to 16° C. for 40 minutes and cooled to $-30°$ C., followed by adding dropwise 40 ml of ethanol at $-30°$ to $-20°$ C. The resultant solution was warmed to room temperature, and stirred under ice-cooling for 3.0 hours after the addition of 300 ml of methylene chloride, 100 ml of ether and 70 ml of ether saturated with water. The crystals separated out were recovered by filtration, washed with ether and dried, thereby affording 3.77 g (86.0% of purity as determined by high performance liquid chromatography, 88.9% of yield) of 7-amino-3-(1-methyl-1H-tetrazol-5-yl)thiomethyl-3-cephem-4-carboxylic acid hydrochloride.

IR(KBr): cm$^{-1}$ 3100 to 2500, 1775, 1715, 1635, 1602.

NMR(DMSO-d$_6$)δ: 3.78(2H,s,2—CH$_2$), 3.97(3H,s,N—CH$_3$), 4.24 and 4.51(2H,ABq,J=14 Hz,3—CH$_2$), 5.13(2H,s,C$_6$—H and C$_7$—H), 8.00 to 10.5 (4H,broad,—$\overset{+}{\text{NH}_3}$ & COOH)

EXAMPLE 3

(1) A 30 ml portion of acetonitrile was added to 5.44 g of 7-ACA and 4.50 g of 5-mercapto-1-(2-N,N-dimethylaminoethyl)-1H-tetrazole, and 29.7 g of DCPA was added through a dropping funnel to the mixture with stirring and under cooling at $-25°$ to $-15°$ C., followed by rinsing the funnel with 2 ml of acetonitrile. The solution produced by returning the inner temperature to 0° C. was stirred at 30° C. for 30 minutes to allow the reaction to proceed. The reaction solution was cooled to $-30°$ C., and warmed to room temperature after the addition of 80 ml of ethanol at $-30°$ to $-20°$ C., followed by stirring for 20 minutes. 600 ml of methylene chloride was added to the solution under ice-cooling, followed by stirring for 1.0 hour. The precipitate was recovered by filtration, washed with 400 ml of methylene chloride and dried, thereby affording 10.87 g (77.5% of purity as determined by high performance liquid chromatography, 91.9% of yield) of 7-amino-3-[1-(2-N,N-dimethylaminoethyl)-1H-tetrazol-5-yl]thiomethyl-3-cephem-4-carboxylic acid dihydrochloride as white powder.

IR(KBr): cm$^{-1}$ 3380, 3200 to 2300, 1792, 1715, 1627.

NMR(D$_2$O)δ: 3.05(6H,s,CH$_3$×2), 3.84(2H,t,J=6 Hz,—CH$_2$—N), 3.85(2H,s,2—CH$_2$), 4.33(2H,s,3—CH$_2$), 4.94(2H,t,J=6 Hz,N—CH$_2$—), 5.16(1H,d,J=5 Hz,C$_6$—H), 5.32(1H,d,J=5 Hz,C$_7$—H).

(2) In 10 ml of water was dissolved 1.0 g of the dihydrochloride as obtained in (1), and the solution was passed through a column packed with 22 ml of Amberlite IR-45 (OH type) at a rate of about 2 ml/min., followed by conducting elution with water. 7 ml of the initial eluate was discarded, and 50 ml of the subsequent eluate was lyophilized, thereby yielding 0.52 g of 7- amino-3-[1-(2-N,N-dimethylaminoethyl)-1H-tetrazol-5-yl]thiomethyl-3-cephem-4-carboxylic acid.

IR(KBr): cm$^{-1}$ 3350, 2920, 1770, 1610.

NMR(D$_2$O)δ: 3.02(6H,s,N—CH$_3$), 3.35 and 3.85(2H,ABq,J=13 Hz,2—CH$_2$). 3.80(2H,t,J=6 Hz,—CH$_2$N), 4.19(2H,ABq,J=14 Hz,3—CH$_2$), 4.87(1H,t,J=6 Hz,N—CH$_2$—), 4.85(1H,d,J=5 Hz,C$_6$—H), 5.05(1H,d,J=5 Hz,C$_7$—H).

(3) In 85 ml of methylene chloride was suspended 5.43 g of the dihydrochloride as obtained in (1) and the suspension was warmed under stirring to distill off 17 ml of methylene chloride. The suspension was cooled to −30° C. and 7.8 ml of di-n-butylamine was added dropwise. The mixture was stirred at −15° to −10° C. and cooled at −30° C. again, and 16 ml of a solution of 4-chloro-3-oxo-butyryl chloride in methylene chloride (2.28 mol/l) was added to it, followed by warming the mixture to 0° C. 17.1 ml of 2 N-HCl was added, and the resultant solution was stirred and separated. The water layer was washed with methylene chloride, and to the water layer were added 1.94 g of thiourea and 60 ml of acetone, and furthermore 77 ml of acetone 4 hours later. The mixture was stirred for 1.0 hour and allowed to stand at 5° to 10° C. for 2 days. The precipitated crystals were recovered by filtration, washed with a mixed solution of 3.6 ml of 2 N-HCl and 48 ml of acetone and then with 50 ml of acetone, air-dried and dried under reduced pressure, thereby affording 4.96 g (90.8% of purity as determined by high performance liquid chromatography, 7.3% of moisture content by the Karl-Fischer method, 81.9% of yield) of slightly yellowish white crystals of 7-[2-(2-aminothiazol-4-yl)acetamido]-3-[1-(2-N,N-dimethylaminoethyl)-1H-tetrazol-5-yl]thiomethyl-3-cephem-4-carboxylic acid dihydrochloride.

EXAMPLE 4

(1) A 8.0 ml portion of nitromethane was admixed with 1.36 g of 7-ACA and 1.13 g of 5-mercapto-1-(2-N,N-dimethylaminoethyl)-1H-tetrazole, and 6.07 g of DCPA was added dropwise to the mixture with stirring and under cooling at −10° to −5° C., followed by allowing the reaction to proceed at 40° C. for 25 minutes. The reaction solution was cooled and 25 ml of n-propanol was added at −30° to −20° C., followed by stirring at 15° to 20° C. for 30 minutes. The solution was cooled again to 5° to 10° C., and 150 ml of methylene chloride was added, followed by stirring for about 1 hour. The resultant precipitate was recovered by filtration, washed with methylene chloride and dried, thereby affording 2.77 g (77.0% of purity as determined by high performance liquid chromatography, 93.1% of yield) of white powder of 7-amino-3-[1-(2-N,N-dimethylaminoethyl)-1H-tetrazol-5-yl]-thiomethyl-3-cephem-4-carboxylic acid dihydrochloride. The NMR and IR values of the product were in accordance with those of the product as obtained in Example 3(1).

(2) The procedure was carried out in the same manner as in (1) while utilizing 8.0 ml of ethyl acetate in place of 8.0 ml of nitromethane as in the above-mentioned (1), and there was obtained 2.72 g (76.8% of purity as determined by high performance liquid chromatography, 91.2% of yield) of 7-amino-3-[1-(2-N,N-dimethylaminoethyl)-1H-tetrazol-5-yl]thiomethyl-3-cephem-4-carboxylic acid dihydrochloride. The IR and NMR values of the product were in accordance with those of the product as obtained in Example 3(1).

EXAMPLE 5

A 8.0 ml portion of acetonitrile was added to 1.36 g of 7-ACA and 1.54 g of 2-ethoxycarbonylmethylthio-5-mercapto-1,3,4-thiadiazole, and the mixture was cooled to −40° to −30° C., followed by adding thereto dropwise 5.40 g of DCPA under stirring. The external bath was removed and the reaction mixture was stirred for 8 minutes, then warmed at 40° C. and stirred for 20 minutes to allow the reaction to proceed. The reaction solution was poured into 10 ml of ice-water, which was adjusted to pH 4.4 with 25% aqueous ammonia. The precipitated powder was recovered by filtration, washed with water and dried, thereby affording 2.08 g (92.7% of yield) of 7-amino-3-[(2-ethoxycarbonylmethylthio-1,3,4-thiadiazol-5-yl)thiomethyl]-3-cephem-4-carboxylic acid in the form of mud yellow powder.

IR(KBr): cm$^{-1}$ 3420, 3150, 3000, 1800, 1733, 1620, 1535.

NMR(D$_2$O+CF$_3$COOD)δ: 1.26(3H,t,J=7 Hz,—CH$_3$), 3.78(2H,s,2—CH$_2$), 3.90 to 4.60(6H,m,CH$_2$×3), 5.18(1H,d,J=5 Hz,C$_6$—H), 5.30(1H,d,J=5 Hz,C$_7$—H).

EXAMPLE 6

While utilizing 0.680 g of 7-ACA, 0.900 g of 5-mercapto-2-morpholinocarbonylmethylthio-1,3,4-thiadiazole, 4.0 ml of acetonitrile and 2.70 g of DCPA, the procedure was carried out in accordance with Example 5, and there was obtained 1.02 g (83.3% of yield) of red brown powder of 7-amino-3-[(2-morpholinocarbonylmethylthio-1,3,4-thiadiazol-5-yl)thiomethyl]-3-cephem-4-carboxylic acid.

IR(KBr): cm$^{-1}$ 3420, 3140, 2900, 1785, 1620, 1535.

NMR(D$_2$O+CF$_3$COOD)δ: 3.72 and 3.79(10H, two lines of s,2—CH$_2$ and

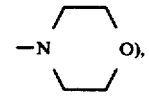

4.26 and 4.56(2H,ABq,J=14 Hz,3—CH$_2$), 4.31(2H,s,—S—CH$_2$CO—), 5.17(1H,d,J=5 Hz,C$_6$—H), 5.32(1H,d,J=5 Hz,C$_7$—H).

EXAMPLE 7

A 3.5 ml portion of acetonitrile was added to 0.570 g of dihydrate of 5-mercapto-1-methyl-1H-tetrazole sodium salt and 0.680 g of 7-ACA, and 1.64 g of diphosphoryl tetrachloride was added dropwise to the mixture under cooling over an external bath at −30° to −20° C., followed by adding 2.29 g of DCPA and rinsing with 0.5 ml of acetonitrile. The reaction solution was stirred at −5° to 0° C. for 5 minutes, warmed at 25° C., and stirred for 40 minutes to allow the reaction to proceed. The reaction solution was cooled and poured into ice-water, which was placed in a refrigerator overnight. The mixture was adjusted to pH 4.0 with 25% aqueous ammonia, and the resultant precipitate was recovered by filtration, washed with cold water and acetone successively and dried, thereby affording 0.732 g (89.3% of yield) of 7-amino-3-(1-methyl-1H-tetrazol-5-yl)thiomethyl-3-cephem-4-carboxylic acid. The NMR values of the product were in accordance with those of the authentic sample.

EXAMPLE 8

A 14.8 g quantity of DCPA was cooled at 14° C., and 1.59 g of 5-mercapto-2-methyl-1,3,4-thiadiazole was added to it, whereby the mixture reached at the temperature of 25° C. and dissolved. 6.0 ml of acetonitrile was added and the solution was cooled at 15° C., to which 2.72 g of 7-ACA and 10.0 ml of acetonitrile were added, followed by stirring at 25° to 27° C. for 30 minutes. The reaction solution was poured into 80 g of ice-water, which was placed in a refrigerator overnight, adjusted to pH 4.0 with 25% aqueous ammonia and stirred for 1.0 hour under ice-cooling. The resultant precipitate was recovered by filtration, washed with 50 ml each of cold water and acetone successively, and dried, thereby affording 2.40 g of 7-amino-3-[(2-methyl-1,3,4-thiadiazol-5-yl)thiomethyl]-3-cephem-4-carboxylic acid.

IR(KBr): $cm^{-1}$ 3470, 3120, 2980, 1795, 1620, 1540.
NMR($D_2O+CF_3COOD$)δ: 2.90(3H,s,—$CH_3$), 3.80(2H,s,2—$CH_2$), 4.33 and 4.70(2H,ABq,J=14 Hz,3—$CH_2$), 5.19(1H,d,J=5 Hz,$C_6$—H), 5.30(1H,d,J=5 Hz,$C_7$—H).

The filtrate and washings were placed in a refrigerator overnight and there was obtained 0.45 g of the second crystals (82.8% of total yield)

EXAMPLE 9

A 14.9 g quantity of DCPA was cooled at 0° C., and 1.84 g of 2-mercaptobenzothiazole and 8.0 ml of acetonitrile were added to it with stirring to a solution. 2.72 g of 7-ACA and 10.0 ml of acetonitrile were added to the solution, and the reaction solution was stirred at 15° to 17° C. for 40 minutes, and cooled at −20° C., followed by adding dropwise 40 ml of ethanol. 300 ml of ether was added to the solution under stirring at about 10° C., and the precipitate was recovered by filtration 30 minutes later, washed with ether and dried, thereby affording 5.26 g of hydrochloride salt of the objective compound. 5.15 g of the product was suspended in 80 ml of water, and the suspension was adjusted to pH 4.0 with aqueous N-NaOH. The precipitate was recovered by filtration, washed with water and dried, thereby affording 3.17 g (85.3% of yield) of the objective compound, 7-amino-3-[(benzothiazol-2-yl)thiomethyl]-3-cephem-4-carboxylic acid.

IR(KBr): $cm^{-1}$ 3300, 3140, 3000, 2600, 1795, 1620, 1545.
NMR($D_2O+CF_3COOD$)δ: 3.88(2H,s,2—$CH_2$), 4.62 and 4.91(2H,ABq,J=14 Hz,3—$CH_2$), 5.34(2H,s,$C_6$—H and $C_7$—H), 7.40 to 8.15

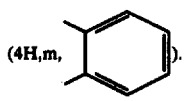
(4H,m,

EXAMPLE 10

A 3.5 ml portion of acetonitrile was added to 0.946 g of 7-amino-3-(2-carboxybenzoyloxy)methyl-3-cephem-4-carboxylic acid and 0.32 g of 5-mercapto-1-methyl-1H-tetrazole, and the mixture was cooled over a dry-ice/ethanol bath, followed by adding through a dropping funnel 3.71 g of DCPA to it with stirring and rinsing the funnel with 1.0 ml of acetonitrile. The external bath was removed, and the reaction mixture was warmed to 0° C., whereby the starting materials dissolved. The solution was stirred at 14° to 16° C. for 40 minutes to allow the reaction to proceed, and the reaction solution was cooled with ice, and poured into ice-water, which was placed in a refrigerator overnight. The precipitate was filtered out and washed with 10 ml of water, and the filtrate and washing were combined and adjusted to pH 4.0 with 25% aqueous ammonia under ice cooling. The precipitated powder was recovered by filtration, washed with water and acetone successively, and dried, thereby affording 0.710 g (86.5% of yield) of 7-amino-3-(1-methyl-1H-tetrazol-5-yl)thiomethyl-3-cephem-4-carboxylic acid. The IR and NMR values of the product were in accordance with those of the authentic sample.

EXAMPLE 11

A 3.5 ml portion of acetonitrile was added to 0.786 g of 7-amino-3-(3-oxobutyryloxy)methyl-3-cephem-4-carboxylic acid and 0.56 g of 5-mercapto-1-(2-N,N-dimethylaminoethyl)-1H-tetrazole, and the mixture was cooled at −30° to −20° C., followed by adding through a dropping funnel 4.05 g of DCPA to it under stirring and rinsing the funnel with 1.0 ml of acetonitrile. When the internal temperature was increased at 0° C., there dissolved the starting materials. The solution was stirred at 28° to 32° C. for 30 minutes to allow the reaction to proceed. The reaction solution was cooled at −30° to −20° C., and 10 ml of ethanol was added dropwise to it. The solution was warmed to 0° C. and placed in a refrigerator overnight, followed by adding 75 ml of methylene chloride. The precipitated powder was recovered by filtration, washed with methylene chloride and dried, thereby affording 1.37 g (78.0% of purity as determined by high performance liquid chromatography, 93.3% of yield) of white powder of 7-amino-3-[1-(2-N,N-dimethylaminoethyl)-1H-tetrazol-5-yl]thiomethyl-3-cephem-4-carboxylic acid dihydrochloride. The IR and NMR values of the product were in accordance with those of the product as obtained in Example 3(1).

EXAMPLE 12

A 7.0 ml portion of acetonitrile was added to 1.64 g of tert-butyl 7-aminocephalosporanate and 0.64 g of 5-mercapto-1-methyl-1H-tetrazole to a solution, and 7.4 g of DCPA was added through a dropping funnel to the solution with stirring under cooling at −10° to 0° C., followed by rinsing the funnel with 1.0 ml of acetonitrile. The reaction solution was stirred at 14° to 16° C. for 40 minutes and subjected to the post treatment by the same procedure as in Example 1, thereby affording 1.36 g (83% of yield) of 7-amino-3-(1-methyl-1H-tetrazol-5-yl)thiomethyl-3-cephem-4-carboxylic acid. The IR and NMR values of the product were in accordance with those of the authentic sample.

EXAMPLE 13

A 6.5 ml portion of acetonitrile was added to 1.36 g of 7-ACA and 0.92 g of 4-methyl-2-thiouracil, and 5.4 g of DCPA was added to the mixture, followed by rinsing with 1.5 ml of acetonitrile. The reaction mixture was stirred at 40° C. for 20 minutes to allow the reaction to proceed. The reaction solution was cooled with ice and poured into 10 ml of ice-water, which was adjusted to pH 4.0 with 25% aqueous ammonia. The precipitate was recovered by filtration, washed with water and dried, thereby affording 1.63 g (92% of yield) of mud yellow powder of 7-amino-3-[(4-methyluracil-2-yl)thiomethyl]-3-cephem-4-carboxylic acid.

IR(KBr): cm$^{-1}$ 3400(sh), 2950, 1780, 1645, 1400, 1350.

NMR(D$_2$O+CF$_3$COOD)$\delta$: 2.54(3H,s,—CH$_3$), 3.84(2H,s,2—CH$_2$), 4.60(2H,ABq,J=14 Hz,3—CH$_2$), 5.21(1H,d,J=5 Hz,C$_6$—H), 5.31(1H,d,J=5 Hz,C$_7$—H), 6.64(1H,s, 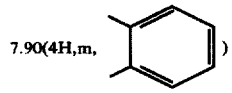—H).

EXAMPLE 14

A 4.0 ml portion of acetonitrile was added to 0.826 g of 7-amino-3-(3-carboxypropionyloxy)methyl-3-cephem-4-carboxylic acid and 0.32 g of 5-mercapto-1-methyl-1H-tetrazole, and 3.71 g of DCPA was added through a dropping funnel to the mixture under cooling at −5° to 0° C., followed by rinsing the funnel with 0.5 ml of acetonitrile. The mixture was stirred at the same temperature and turned into a solution. Then, the reaction solution was stirred for 45 minutes at 14° to 15° C. to allow the reaction to proceed. The reaction solution was cooled with ice, and poured into ice-water, which was placed in a refrigerator overnight and adjusted to pH 4.0 with 25% aqueous ammonia. The precipitated powder was recovered by filtration, washed with water and acetone successively, and dried, thereby affording 0.722 g (88.0% of yield) of 7-amino-3-(1-methyl-1H-tetrazol-5-yl)thiomethyl-3-cephem-4-carboxylic acid. The IR and NMR values of the product were in accordance with those of the authentic sample.

EXAMPLE 15

A 1.66 g quantity of 2-mercaptobenzoxazole, 18 ml of acetonitrile and 2.72 g of 7-ACA were added to 14.9 g of DCPA with stirring under cooling at 10° C., and the reaction was allowed to proceed at 15° to 17° C. for 40 minutes. The reaction solution was cooled with ice and poured into 120 g of ice-water. The precipitate was recovered by filtration, washed with water (20 ml×4) and acetone successively, and dried thereby affording 3.35 g (92.3% of yield) of 7-amino-3-[(benzoxazol-2-yl)thiomethyl]-3-cephem-4-carboxylic acid.

Elemental analysis (for C$_{15}$H$_{13}$N$_3$S$_2$O$_4$.0.3H$_2$O): Found: C, 48.83; H, 3.59; N, 11.27; Calcd.: C, 48.85; H, 3.72; N, 11.39.

NMR(D$_2$O+CF$_3$COOD)$\delta$: 3.88(2H,s,2—CH$_2$), 4.75(2H,s,3—CH$_2$), 5.30(2H,s,C$_6$—H and C$_7$—H), 7.50 to 7.90(4H,m, )

EXAMPLE 16

In 8.0 ml of acetonitrile were suspended 1.36 g of 7-ACA and 1.13 g of 5-mercapto-1-(2-N,N-dimethylaminoethyl)-1H-tetrazole, and 0.40 g of water was added to the suspension. The mixture was cooled to −40° C. under stirring, and 5.67 g of diphosphoryl tetrachloride was added dropwise at −40° to −30° C. After the dropwise addition, the cooling bath was removed, and the mixture was stirred for about 5 minutes and then placed in a warm bath at 40° C., followed by stirring for 20 minutes. The reaction solution was cooled, and 20 ml of acetonitrile and then 6.0 ml of an ether solution of hydrogen chloride (5.5 mol/l of the HCl concentration) and 150 ml of ether were added. The precipitated powder was recovered by filtration and washed with a mixed solution of acetonitrile and ether and then with ether. Upon drying, there was obtained 3.32 g (65.6% of purity; 95.0% of yield) of 7-amino-3-[1-(2-N,N-dimethylaminoethyl)-1H-tetrazol-5-yl]thiomethyl-3-cephem-4-carboxylic acid dihydrochloride.

IR(KBr): $\beta$-lactam 1780 cm$^{-1}$.

NMR(D$_2$O)$\delta$: ppm 3.08(6H,s), 3.88(2H,s), 3.83(2H,t,J=6 Hz,), 4.38(2H,s), 4.96(2H,t,J=6 Hz), 5.18(1H,d,J=5 Hz), 5.36(1H,d,J=5 Hz).

EXAMPLE 17

In 8 ml of acetonitrile were suspended 1.57 g of 7-amino-3-(3-oxobutyryloxy)methyl-3-cephem-4-carboxylic acid, 0.50 g of water and 1.13 g of 5-mercapto-1-[2-(N,N-dimethylamino)ethyl]-1H-tetrazole, and the suspension was cooled at −20° C. 6.93 g of diphosphoryl tetrachloride was added dropwise to the suspension under stirring at −20° to −15° C. The cooling bath was removed, and the reaction mixture was stirred for 5 minutes and placed in a warm bath at 30° C., followed by stirring for 45 minutes. The reaction solution was cooled and 100 ml of acetonitrile and 10 ml of water were added, followed by the addition of triethylamine to adjust the solution to pH 5.4. The resultant precipitate was recovered by filtration and dried under reduced pressure, thereby affording 2.43 g (78.2% of purity; 90.1% of yield) of 7-amino-3-[1-(2-N,N-dimethyl-aminoethyl)-1H-tetrazol-5-yl]-thiomethyl-3-cephem-4-carboxylic acid hydrochloride.

IR(KBr): $\beta$-lactam 1795 cm$^{-1}$.

NMR(D$_2$O)$\delta$ ppm: 3.09(6H,s,), 3.82(2H,s), 3.87(2H,t,J=6 Hz), 4.16 and 4.42(2H,ABq,J=14 Hz), 4.94(2H,t,J=6 Hz), 5.16(1H,d,J=5 Hz), 5.30(1H,d,J=5 Hz).

EXAMPLE 18

(1) In 24.0 ml of acetonitrile were suspended 1.36 g of 7-ACA and 1.13 g of 5-mercapto-1-(2-N,N-dimethylaminoethyl)-1H-tetrazole, and 0.41 g of water was added, followed by cooling at 15° to 20° C. 5.67 g of diphosphoryl tetrachloride was added dropwise to the mixture with stirring at the same temperature. After the dropwise addition, the reaction solution was stirred at 20° C. for 5 minutes and then at 30° C. for 45 minutes, and cooled. 100 ml of acetonitrile and then 10 ml of cold water were added, and triethylamine was added to adjust the solution to pH 5.4. The resultant precipitate was recovered by filtration, washed with acetonitrile and dried, thereby affording 2.51 g (77.9% of purity; 92.6% of yield) of 7-amino-3-[1-(2-N,N-dimethylaminoethyl)-1H-tetrazol-5-yl]thiomethyl-3-cephem-4-carboxylic acid hydrochloride. The IR and NMR values of the product were in accordance with those of the compouned obtained in Example 17.

(2) While utilizing the solvents described below in place of 24.0 ml of acetonitrile used as a reaction solvent under the item (1), diphosphoryl tetrachloride was added dropwise at −20° to −30° C. and the reaction mixture was stirred at −20° to 0° C. for 5 minutes after the dropwise addition. The reaction mixture was warmed at 40° C. for the length of time described below to allow the reaction to proceed. The reaction solution was treated in the same manner as under the item (1), and the results obtained are shown in the following:

| No. | Kind of solvent | Amount of solvent | Warming time | Yield |
|---|---|---|---|---|
| 1 | Nitromethane | 8.0 ml | 20 min | 93.4% |
| 2 | Ethyl acetate | 8.0 ml | 30 min | 91.3% |

In 5.4 ml of acetonitrile were suspended 0.909 g of 7-ACA and 0.504 g of 5-mercapto-1-methyl-1H-tetrazole, and 0.256 g of water was added. The suspension was cooled at −40° C. under stirring, and 3.58 g of diphosphoryl tetrachloride was added dropwise to it at −50° to −35° C. The reaction mixture was stirred at −35° to 0° C. for 5 minutes after the dropwise addition and placed in a warm water bath at 40° C. to warm, followed by stirring at the same temperature for 20 minutes. The reaction solution was cooled over an ice water bath and, after the addition of 11 ml of cold water, it was adjusted to pH 4.0 with aqueous concentrated ammonia. The separated-out precipitate was recovered by filtration, washed with water and dried, thereby affording 0.956 g of 7-amino-3-(1-methyl-1H-tetrazol-5-yl)thiomethyl-3-cephem-4-carboxylic acid. The yield was 87.2%.

IR(KBr): $\beta$-lactam 1790 cm$^{-1}$.

NMR(D$_2$O+CF$_3$CO$_2$D)$\delta$ ppm value: 3.74(2H,s), 4.09(3H,s), 4.36(2H,s), 5.17(1H,d,J=5 Hz), 5.31(1H,d,J=5 Hz).

EXAMPLE 20

In 4 ml of acetonitrile were suspended 1.89 g of ethyl 7-amino-3-(3-oxobutyryloxy)methyl-3-cephem-4-carboxylate hydrochloride and 0.75 g of 5-mercapto-1-methyl-1H-tetrazole, and 0.18 g of water was added. 2.52 g of diphosphoryl tetrachloride was added dropwise to the suspension under stirring at −30° to −20° C. The reaction solution was stirred at −20° to 0° C. for 5 minutes and then at 30° C. for 45 minutes, cooled at 5° C., and poured into 50 ml of an ether solution of hydrogen chloride (0.1 mol/l of HCl concentration). The deposited powder was recovered by filtration and washed with ether. 15 ml of water was added to the powder, and sodium hydrogencarbonate was addded to the mixture under ice-cooling. The mixture was adjusted to pH 7.0 and was extracted with 20 ml and 15 ml portions of methylene chloride. The methylene chloride layer was dried over magnesium sulfate, and the solvent was distilled off. The residue was dissolved in ethyl acetate, and a solution of p-toluenesulfonic acid monohydrate in a mixture of methanol and ethyl acetate was added to the solution. The deposited crystals were recovered by filtration and dried, thereby affording 2.25 g (85.1% of yield) of ethyl 7-amino-3-(1-methyl-1H-tetrazol-5-yl)thiomethyl-3-cephem-4-carbonate.p-toluenesulfonate.

IR(KBr): $\beta$-lactam 1790 cm$^{-1}$; ester 1730 cm$^{-1}$.

NMR(CDCl$_3$)$\delta$ ppm: 1.24(3H,t,J=7 Hz), 2.31(3H,s), 3.81(3H,s), 3.95 to 4.25(5H,m), 4.98(1H,d,J=5 Hz), 5.22(1H,d,J=5 Hz), 6.25(1H,s), 7.08 and 7.72(4H,ABq,J=9 Hz).

EXAMPLE 21

Mixed were 0.68 g of 7-ACA, 0.18 g of water and 0.90 g of 5-mercapto-2-morpholinocarbonylmethylthio-1,3,4-thiadiazole, and 4.0 ml of acetonitrile was added to the mixture, 2.52 g of diphosphoryl tetrachloride was added to the mixture under stirring in a dry ice/acetone bath at −20° to −40° C. over a period of about 10 minutes, and the cooling bath was removed. After the temperature was allowed to increase at 0° C., the reaction solution was stirred in a warm water bath at 40° C. for 20 minutes, cooled with ice and adjusted to pH 4.3 with aqueous concentrated ammonia following the addition of 5 ml of water. There was obtained 1.10 g (89.9% of yield) of 7-amino-3-(2-morpholinocarbonylmethylthio-1,3,4-thiadiazol-5-yl)thiomethyl-3-cephem-4-carboxylic acid thus produced.

IR(KBr): $\beta$-lactam 1785 cm$^{-1}$.

NMR(D$_2$O+CF$_3$COOD)$\delta$ ppm: 3.74(8H,broad), 3.79(2H,s), 4.15 to 4.68(4H,m), 5.17(1H,d,J=5 Hz), 5.32(1H,d,J=5 Hz).

EXAMPLE 22

Mixed were 1.36 g of 7-ACA, 0.36 g of water and 1.32 g of 2-dimethylaminocarbonylmethyl-5-mercapto-1,3,4-thiadiazole, and 6.5 ml of acetonitrile was added. 5.04 g of diphosphoryl tetrachloride was added through a dropping funnel to the mixture at −20° to −30° C., followed by rinsing the funnel with 1.5 ml of acetonitrile. The reaction mixture was warmed at 10° C. over a period of 5 minutes with stirring, placed in a warm water bath of 40° C. and stirred at the same temperature for 20 minutes. The reaction solution was cooled with ice and adjusted to pH 4.1 with aqueous concentrated ammonia after the addition of 10 ml of cold water. The precipitate was recovered by filtration, washed with water and dried, thereby affording 1.82 g (87.6%) of 7-amino-3-(2-dimethylaminocarbonylmethyl-1,3,4-thiadiazol-5-yl)thiomethyl-3-cephem-4-carboxylic acid.

IR(KBr): $\beta$-lactam 1790 cm$^{-1}$.

NMR(D$_2$O+CF$_3$COOD)$\delta$ ppm: 3.05(s,3H), 3.15(3H,s), 3.81(2H,s), 4.54(2H,broad), 5.19(1H,d,J=5 Hz), 5.31(1H,d,J=5 Hz).

EXAMPLE 23

The procedure was carried out in accordance with Example 22, while utilizing 0.41 g of 7-ACA, 0.11 g of water, 2.4 ml of acetonitrile, 0.46 g of 2-(2-acetoxy)ethylthio-5-mercapto-1,3,4-thiadiazole and 1.51 g of diphosphoryl tetrachloride, and there was obtained 0.61 g (90.7%) of 7-amino-3-[2-(2-acetoxy)ethylthio-1,3,4-thiadiazol-5-yl]thiomethyl-3-cephem-4-carboxylic acid.

IR(KBr): $\beta$-lactam 1795 cm$^{-1}$; ester 1740 cm$^{-1}$.

NMR(D$_2$O+CF$_3$COOD)$\delta$ ppm: 2.08(s,3H), 3.53(2H,t,J=6 Hz), 3.79(2H,s), 4.18 to 4.79(4H,m), 5.19(1H,d,J=5 Hz), 5.30(1H,d,J=5 Hz).

EXAMPLE 24

The procedure was carried out in accordance with Example 22, while utilizing 1.36 g of 7-ACA, 0.36 g of water, 8.0 ml of acetonitrile, 1.54 g of 2-ethoxycarbonylmethylthio-5-mercapto-1,3,4-thiadiazole and 5.04 g of diphosphoryl tetrachloride, and there was obtained 2.06 g (91.8%) of 7-amino-3-(2-ethoxycarbonylmethylthio-1,3,4-thiadiazol-5-yl)thiomethyl-3-cephem-4-carboxylic acid.

IR(KBr): $\beta$-lactam 1800 cm$^{-1}$; ester 1730 cm$^{-1}$.

NMR(D$_2$O+CF$_3$COOD)$\delta$ ppm: 1.27(3H,t,J=7 Hz), 3.79(2H,s), 4.07(2H,s), 4.26(2H,q,J=7 Hz), 4.46(2H,broad), 5.20(1H,d,J=5 Hz), 5.30(1H,d,J=5 Hz).

EXAMPLE 25

The procedure was carried out in accordance with Example 22, while utilizing 0.68 g of 7-ACA, 0.20 g of water, 5.0 ml of acetonitrile, 0.87 g of 2-(2-sulfo)ethylthio-5-mercapto-1,3,4-thiadiazole sodium salt and 2.83 g of diphosphoryl tetrachloride, and there was obtained 1.04 g (84.5%) of monosodium 7-amino-3-[2-(2-sulfo)ethylthio-1,3,4-thiadiazol-5-yl]thiomethyl-3-cephem-4-carboxylate.

IR(KBr): $\beta$-lactam 1790 cm$^{-1}$.

NMR(D$_2$O+CF$_3$COOD)$\delta$ ppm: 3.2 to 3.9(4H,m), 3.80(2H,s), 3.39(2H,broad), 5.19(1H,d,J=5 Hz), 5.31(1H,d,J=5 Hz).

EXAMPLE 26

In 8 ml of acetonitrile was dissolved 1.64 g of tertbutyl 7-aminocephalosporanate, and after the addition of 0.36 g of water and 0.75 g of 5-mercapto-1-methyl-1H-tetrazole, the solution was cooled. 5.03 g of diphosphoryl tetrachloride was added dropwise to the solution with stirring at $-20°$ to $-30°$ C. After the dropwise addition, the cooling bath was removed, and the reaction solution was stirred for 3 minutes, warmed on a warm-water bath of 40° C. and stirred at the same temperature for 20 minutes. The reaction solution was cooled with ice and adjusted to pH 4.0 with aqueous concentrated ammonia after the addition of 10 ml of ice-water. The precipitate was recovered by filtration, washed with cold water and dried, thereby affording 1.34 g (81.7% of yield) of 7-amino-3-(1-methyl-1H-tetrazol-5-yl)thiomethyl-3-cephem-4-carboxylic acid. The IR and NMR values of the product were in accordance with those of the product as obtained in Example 19.

EXAMPLE 27

A 12.59 g portion of diphosphoryl tetrachloride was cooled at $-30°$ to $-40°$ C., and 0.90 g of water was added to it under stirring at the same temperature. The mixture was warmed to 0° C., and 1.13 g of 5-mercapto-1-(2-N,N-dimethylaminoethyl)-1H-tetrazole and then 1.36 g of 7-ACA were added. The resultant mixture was warmed to 40° C. and stirred at the same temperature for 15 minutes. The reaction solution was cooled with ice, and after 100 ml of acetonitrile and then 10 ml of water were added, it was adjusted to pH 5.5 by adding triethylamine little by little. The precipitate was recovered by filtration, washed with acetonitrile and dried, thereby affording 2.05 g (62.5% of purity, 60.7% of yield) of 7-amino-3-[1-(2-N,N-dimethylaminoethyl)-1H-tetrazol-5-yl]thiomethyl-3-cephem-4-carboxylic acid hydrochloride. The IR and NMR values of the product were in accordance with those of the product as obtained in Example 17.

EXAMPLE 28

In 10 ml of acetonitrile was suspended 1.89 g of 7-amino-3-(2-carboxybenzoyloxy)methyl-3-cephem-4-carboxylic acid, and 0.52 g of water was added, followed by cooling. 7.24 g of diphosphory tetrachloride was added dropwise to the mixture under stirring at $-50°$ to $-30°$ C., and the mixture was warmed to 0° C. over a period of about 5 minutes, followed by the addition of 1.13 g of 5-mercapto-1-(2-N,N-dimethylaminoethyl)-1H-tetrazole. The resultant mixture was warmed at 30° C. for 45 minutes, stirred and cooled. After 100 ml of acetonitrile and then 10 ml of water were added, it was adjusted to pH 5.4 by the addition of triethylamine. The resulting precipitate was recovered by filtration, washed with acetonitrile and dried, thereby affording 2.46 g (77.9% of purity; 90.8% of yield) of 7-amino-3-[1-(2-N,N-dimethylaminoethyl)-1H-tetrazol-5-yl]thiomethyl-3-cephem-4-carboxylic acid hydrochloride. The IR and NMR values of the product were in accordance with those of the product as obtained in Example 17.

EXAMPLE 29

By the same procedure as in Example 28, wherein 1.65 g of 7-amino-3-(3-carboxypropionyloxy)methyl-3-cephem-4-carboxylic acid was used in place of 7-amino-3-(2-carboxybenzoyloxy)methyl-3-cephem-4-carboxylic acid, there was obtained 2.57 g (76.7% of purity, 93.4% of yield) of 7-amino-3-[1-(2-N,N-dimethylaminoethyl)-1H-tetrazol-5-yl]-thiomethyl-3-cephem-4-carboxylic acid hydrochloride. The IR and NMR values of the product were in accordance with those of the product as obtained in Exmaple 17.

EXAMPLE 30

A 75 ml portion of ether was added to 76.1 g of phosphorus oxychloride, and 8.94 g of water was added dropwise to the mixture under stirring at $-30°$ to $-25°$ C., followed by stirring at $-20°$ to $-15°$ C. for 15 minutes to allow the reaction to proceed. The reaction solution was warmed to room temperature, and freed of hydrogen chloride and ether by distillation under reduced pressure, resulting in 67.0 g of colorless, clear DCPA. While, 5.63 g of 7-ACA and 4.5 g of 5-mercapto-1-(2-N,N-dimethylaminoethyl)-1H-tetrazole were suspended in 32 ml of acetonitrile, and 67.0 g of the above-described DCPA was added to the suspension under ice-cooling, followed by warming to room temperature to allow the reaction to proceed at about 30° C. for 60 minutes. The reaction solution was cooled at $-20°$ C., and 100 ml of ethanol and then 750 ml of methylene chloride were added. The precipitated powder was recovered by filtration, washed with methylene chloride and dried, thereby affording 7-amino-3-[1-(2-N,N-dimethylaminoethyl)-1H-tetrazol-5-yl]thiomethyl-3-cephem-4-carboxylic acid dihydrochloride in slightly yellowish brown powder (68.5% of purity, 81.6% of yield). The IR and NMR values of the product were in accordance with those of the product as obtained in Example 3(1).

EXAMPLE 31

In 6 ml of acetonitrile were suspended 1.16 g of pivaloyloxymethyl 7-amino-3-acetoxymethyl-3-cephem-4-carboxylate and 0.68 g of 5-mercapto-1-(2-N,N-dimethylaminoethyl)-1H-tetrazole, and 4.45 g of DCPA was added to the suspension under cooling with ice to make the suspension into a solution, followed by stirring at about 30° C. for 40 minutes to allow the reaction to proceed. 15 ml of acetonitrile was added to the reaction solution, to which an ether solution of hydrogen chloride and ether were added. The precipitated powder was recovered by filtration and suspended in 20 ml of cold water. The suspension was adjusted to pH 7.5 with 40% potassium carbonate and extracted with 100 ml of methylene chloride. The methylene chloride layer was washed with water, dried with magnesium sulfate and concentrated. An ether solution of hydrogen chloride and ether were added to the concentrate, and the precipitated powder was recovered by filtration, washed with ether and dried, thereby affording 1.42 g (82.7% of yield) of pivaloyloxymethyl 7-amino-3-[1-(2-N,N-dimethylaminoethyl)-1H-tetrazol-5-yl]-thiomethyl-3-cephem-4-carboxylate dihydrochloride.

IR(KBr) cm$^{-1}$: 3360, 2940, 2660, 1780, 1746.

NMR(d$_6$-DMSO-D$_2$O)δ ppm: 1.17(9H,s,CH$_3$×3), 3.00(6H,s,N—CH$_3$×2), 3.79(2H,CH$_2$), 3.87(2H,CH$_2$), 4.36(2H,CH$_2$), 4.86(2H,CH$_2$), 5.10(1H,d,J=5 Hz,C$_6$—H), 5.26(1H,d,J=5 Hz,C$_7$—H), 5.85(2H,ABq,J=7 Hz,CH$_2$).

EXAMPLE 32

In 7 ml of acetonitrile were suspended 1.31 g of acetylmethyl 7-amino-3-acetoxymethyl-3-cephem-4-carboxylate and 0.90 g of 5-mercapto-1-(2-N,N-dimethylaminoethyl)-1H-tetrazole, and 5.92 g of DCPA was added to the suspension under ice-cooling to a solution, followed by stirring at 30° C. for 40 minutes to allow the reaction to proceed. 15 ml of acetonitrile, and an ether solution of hydrogen chloride and ether were added to the reaction solution, and the precipitated powder was recovered by filtration and treated in the same manner as in Example 31, thereby affording 1.72 g (83.9% of yield) of acetylmethyl 7-amino-3-[1(2-N,N-dimethylaminoethyl)-1H-tetrazol-5-yl]thiomethyl-3-cephem-4-carboxylate dihydrochloride.

IR(KBr) cm$^{-1}$: 3380, 2900, 2670, 1780, 1724, 1625.

NMR(D$_2$O)δ ppm: 2.24(3H,s,COCH$_3$), 3.05(6H,s,N(CH$_3$)$_2$), 3.84(2H,t,J=6 Hz,—CH$_2$N), 3.89(2H,s,2—CH$_2$), 4.40(2H,s,3—CH$_2$), 4.95(2H,t,J=6 Hz,—CH$_2$N), 4.99(2H,s,—OCH$_2$CO—), 5.17(1H,d,J=5 Hz,C$_6$—H), 5.35(1H,d,J=5 Hz,C$_7$—H).

EXAMPLE 33

A 5 ml portion of acetonitrile was added to 1.16 g of 1-(ethoxycarbonyloxy)ethyl 7-amino-3-acetoxymethyl-3-cephem-4-carboxylate and 0.78 g of 5-mercapto-1-(2-N,N-dimethylaminoethyl)-1H-tetrazole, and 3.7 g of DCPA was added to the mixture with stirring under ice-cooling to a solution, followed by allowing the reaction to proceed at about 30° C. for 40 minutes. The reaction solution was treated in the same manner as in Example 32, thereby affording 1.39 g (80.9% of yield) of 1-(ethoxycarbonyloxy)ethyl 7-amino-3-[1-(2-N,N-dimethylaminoethyl)-1H-tetrazol-5-yl]thiomethyl-3-cephem-4-carboxylate dihydrochloride.

IR(KBr) cm$^{-1}$: 3380, 2860, 2650, 1783, 1763, 1623.

NMR(d$_6$-DMSO)δ ppm: 1.28(3H,t,J=7 Hz,—CH$_3$), 1.55 and 1.59(3H,dd,J=5 Hz,—CH$_3$), 3.08(6H,s,—N(CH$_3$)$_2$), 3.87(2H,t,J=6 Hz,—CH$_2$N), 3.90(2H,s,2—CH$_2$), 4.27(2H,q,J=7 Hz,—CH$_2$OCO—), 4.34(2H,s,3—CH$_2$), 4.97(2H,t,J=6 Hz,—CH$_2$N), 5.17(1H,d,J=5 Hz,C$_6$—H), 5.33(1H,d,J=5 Hz,C$_7$—H), 6.60 to 7.00(1H,m,—CO$_2$CH).

EXAMPLE 34

A 1.36 g quantity of 7-ACA, 2.20 g of 5-mercapto-1-(2-N,N-dimethylaminoethyl)-1H-tetrazole and 1.44 g of methanol were mixed, and 6.5 ml of acetonitrile was added to the mixture. The mixture was cooled at −40° to −35° C., and 11.32 g of diphosphoryl tetrachloride was added dropwise to it under stirring, followed by rinsing with 1.5 ml of acetonitrile. The reaction solution was stirred at the same temperature for 15 minutes, and the reaction was allowed to proceed at 30° C. for 40 minutes. The reaction solution was treated in the same manner as in Example 18(1), and there was obtained 2.30 g (76.1% of purity, 83.0% of yield) of 7-amino-3-[1-(2-N,N-dimethylaminoethyl)-1H-tetrazol-5-yl]thiomethyl-3-cephem-4-carboxylic acid hydrochloride. The IR and NMR values of the product were in accordance with those of the product as obtained in Example 17.

REFERENCE EXAMPLE

In 15 ml of methylene chloride and 10 ml of water was put 514 mg of acetylmethyl 7-amino-3-[1-(2-N,N-dimethylaminoethyl)-1H-tetrazol-5-yl]thiomethyl-3-cephem-4-carboxylate dihydrochloride, and 168 mg of sodium hydrogencarbonate was added. The mixture was stirred, and separated. The methylene chloride layer was taken, and dried over calcium chloride, followed by distilling off the methylene chloride. 15 ml of methylene chloride was added to the residue to make into a solution. The solution was cooled at −25° C., and a solution of 4-chloro-3-oxo-butyryl chloride in methylene chloride (1.54 mM, 2.0 ml) was added. The solution was stirred at −20° to −15° C. for 20 minutes, and 380 mg of thiourea and 5 ml of dimethylacetamide were added, followed by stirring at room temperature for 3 hours. Water was added to the reaction solution, and the water layer was adjusted to pH 6.0 and extracted with methylene chloride. Water was added to the methylene chloride layer, and the mixture was adjusted to pH 1.5 with 4 N—HCl and separated. The water layer was deaerated under reduced pressure and subjected to chromatography with Amberlite XAD-2 (40 ml), whereby the elution was made with 0.01 N—HCl (120 ml) and acetonitrile:0.01 N—HCl (5:95 V/V) successively. The effective eluate determined by means of thin layer chromatography was concentrated, adjusted to pH 6.0 and extracted with methylene chloride. The methylene chloride layer was dried over magnesium sulfate, and an ether solutoin of hydrogen chloride was added. The precipitated powder was recovered by filtration, washed with methylene chloride and dried, thereby affording acetylmethyl 7β-[2-(2-aminothiazol-4-yl)-acetamido]-3-[1-(2-N,N-dimethylaminoethyl)-1H-tetrazol-5-yl]thiomethyl-3-cephem-4-carboxylate dihydrochloride.

IR(KBr)cm$^{-1}$: 3350, 2995, 2670, 1770, 1718, 1670, 1622.

NMR(d$_6$-DMSO)δ ppm: 2.26(3H,s,—COCH$_3$), 3.08(6H,s,—N(CH$_3$)$_2$), 3.76 to 3.96(6H,m,CH$_2$×3), 4.37(2H,s,—CH$_2$—), 4.93(2H,t,N—CH$_2$—), 5.01(2H,s,—OCH$_2$CO—), 5.23(1H,d,C$_6$—H), 5.71(1H,d,C$_7$—H), 6.73(1H,s, 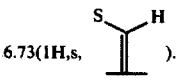 ).

EXPERIMENT EXAMPLE 1

A 0.68 g quantity of 7-ACA was mixed with 0.30 g of 5-mercapto-1-methyl-1H-tetrazole (hereinafter referred to briefly as "TZ"), and 5 ml of acetic acid and 2.89 g of phosphoric acid were added successively. The mixture was warmed at 50±3° C. and stirred for 5 hours to allow the reaction to proceed. The reaction mixture was cooled with ice, and ice-water was added to make the total volume to 50 ml. Quantitative determination by high performance liquid chromatography (HPLC) on 7-amino-3-(1-methyl-1H-tetrazol-5-yl)thiomethyl-3-cephem-4-carboxylic acid (hereinafter referred to briefly as "7ATC") indicated not more than 2% of the formation yield. HPLC was carried out at a flow rate of 0.1 ml/min (34 kg/cm$^2$G), a detector sensitivity of 0.16 AUFS (UV$_{254}$) and a separatory column temperature of 50° C. by adding a 0.05 M aqueous sodium borate solution to a sample (the reaction mixture adjusted to 50 ml as described above) to a uniform solution and diluting with a sodium citrate buffer (pH 5.0) for injection into chromatograph, with Hitachi cation exchange resin #2610, 2.1 mm × 50 cm, utilized as the separatory column and a sodium citrate buffer (pH 5.0) used as mobile phase.

EXPERIMENT EXAMPLES 2 TO 29

The reaction was carried out under the conditions as described in (Table 1), while using different acids in place of phosphoric acid and acetic acid or acetonitrile as reaction solvent in Experiment Example 1, and investigation was made on the formation yield of 7-ATC in the same manner as in Experiment Example 1. There were obtained results as shown in (Table 1).

EXPERIMENT EXAMPLES 30 TO 37

7-ACA or 7-amino-3-(3-oxobutyryloxy)methyl-3-cephem-4-carboxylic acid (hereinafter referred to briefly as "7-ABC") was mixed with 5-mercapto-1-(2-N,N-dimethylaminoethyl)-1H-tetrazole (hereinafter referred to briefly as "MTZ"), and acetonitrile or acetic acid was added as a solvent, followed by adding a variety of acids as acid. Then, the reaction was carried out under the conditions as shown in (Table 2), and the quantitative determination was effected, in the same manner as in Experiment Example 1. Investigation was made on the formation yield of 7-amino-3-[1-(2-N,N-dimethylaminoethyl)-1H-tetrazol-5-yl]thiomethyl-3-cephem-4-carboxylic acid (hereinafter referred to briefly as "7-AMTC"), and there were obtained results as shown in (Table-2). Conditions of the quantitative determination by HPLC were the same as in Experiment 1 with the exception that a flow rate of the mobile phase was changed to 0.25 ml/min. (76 kg/cm$^2$G).

TABLE 1

| Experiment No | Amount of 7-ACA (g) | Amount of TZ (g) | Acid Kind | Amount (g) | Solvent Kind | Amount (ml) | Reaction temperature (°C.) | Reaction time | Formation yield of 7-ATC (%) |
|---|---|---|---|---|---|---|---|---|---|
| 2 | 1.36 | 0.60 | phosphoric acid | 4.04 | acetonitrile | 6.8 | 50 | 1 hr | 0 |
| 3 | 1.36 | 0.60 | pyrophosphoric acid | 6.23 | acetonitrile | 6.8 | 30 | 75 min | 0 |
| 4 | 0.68 | 0.30 | metaphosphoric acid | 2.00 | acetic acid | 5.0 | 50 | 5 hr | 0 |
| 5 | 1.36 | 0.60 | pyrophosphoric acid | 8.90 | acetic acid | 10.0 | 45–50 | 10 hr | 40.8 |
| 6 | 0.68 | 0.30 | boric acid | 1.55 | acetic acid | 5.0 | 50 | 5 hr | 0 |
| 7 | 1.36 | 0.60 | formic acid | 1.61 | acetonitrile | 6.8 | 30 | 75 min | 0 |
| 8 | 1.36 | 0.60 | acetic acid | — | acetic acid | 15 | 45–50 | 10 hr | 0 |
| 9 | 1.36 | 0.60 | acetic acid | 2.10 | acetonitrile | 6.8 | 30 | 75 min | 0 |
| 10 | 1.36 | 0.60 | trifluoroacetic acid | 3.99 | acetonitrile | 6.8 | 30 | 75 min | 0 |
| 11 | 0.54 | 0.28 | propionic acid | 2.96 | acetonitrile | 2.0 | 50 | 3 hr | 0 |
| 12 | 0.54 | 0.28 | o-nitrobenzoic acid | 3.34 | acetonitrile | 6.0 | 50 | 3 hr | 0 |
| 13 | 0.54 | 0.28 | o-chlorophenol | 2.58 | acetonitrile | 6.0 | 50 | 3 hr | 0 |
| 14 | 0.54 | 0.28 | o-nitrophenol | 2.58 | acetonitrile | 6.0 | 50 | 3 hr | 0 |
| 15 | 0.68 | 0.30 | 25% HBr/acetic acid | 8.08 | acetic acid | 4.0 | 50 | 5 hr | 0 |
| 16 | 0.68 | 0.30 | hyrogen chloride | (Note 1) | acetic acid | 5.0 | 50 | 5 hr | 0 |
| 17 | 0.68 | 0.30 | hyrogen chloride | (Note 1) | acetonitrile | 5.0 | 50 | 5 hr | 0 |
| 18 | 1.36 | 0.58 | 2-aminoethane-1-sulfonic acid | 3.75 | acetic acid | 13.5 | 50 | 2.5 hr | 0 |
| 19 | 1.36 | 0.58 | 2-cyanoacetic acid | 2.55 | acetic acid | 13.5 | 50 | 2.5 hr | 0 |
| 20 | 1.36 | 0.58 | benzoic acid | 3.66 | acetic acid | 13.5 | 50 | 2.5 hr | 0 |
| 21 | 1.36 | 0.58 | phthalic acid | 4.98 | acetic acid | 13.5 | 50 | 2.5 hr | 0 |
| 22 | 1.36 | 0.58 | malonic acid | 3.12 | acetic acid | 13.5 | 50 | 2.5 hr | 0 |
| 23 | 1.36 | 0.58 | anhydrous ferric chloride | 2.43 | acetic acid | 13.5 | 50 | 2.0 hr | 12.3 |
| 24 | 1.36 | 0.58 | anhydrous aluminium chloride | 2.00 | acetic acid | 13.5 | 50 | 2.0 hr | 7.4 |
| 25 | 1.36 | 0.58 | phosphorus trichloride | 2.06 | acetic acid | 13.5 | 50 | 78 min | 5.5 |
| 26 | 1.36 | 0.58 | phosphorus trichloride | 2.06 | acetic acid | 13.5 | 30 | 1 hr | 1.2 |
| 27 | 1.36 | 0.58 | phosphorus trichloride | 2.06 | acetonitrile | 7.0 | 30 | 1 hr | 0 |
| 28 | 1.36 | 0.58 | titanium tetrachloride | 2.85 | acetonitrile | 7.0 | 30 | 1 hr | 1.8 |
| 29 | 1.36 | 0.58 | boron tribromide | 3.75 | acetonitrile | 7.0 | 30 | 1 hr | 3.0 |

Note 1
The reaction was conducted under the introduction of dehydrated hydrogen gas into the reaction mixture.

TABLE 2

| Experiment No | Amount of 7-ACA or 7-ABC (g) | Amount of MTZ (g) | Acid Kind | Amount (g) | Solvent Kind | Amount (ml) | Reaction temperature (°C.) | Reaction time | Formation yield of 7-AMTC (%) |
|---|---|---|---|---|---|---|---|---|---|
| 30 | 7-ACA 0.68 | 0.43 | pyropohsphoric acid | 3.00 | acetonitrile | 4.0 | 50 | 100 min | 0 |
| 31 | 7-ACA 0.68 | 0.43 | pyrophosphoric acid phosphorus oxychloride | 3.60 4.60 | acetonitrile | 6.0 | 50 | 1 hr | 0 |
| 32 | 7-ACA 0.68 | 0.43 | diphenylphosphinic acid | 2.93 | acetonitrile | 10.0 | 50 | 40 min | 0 |
| 33 | 7-ACA 0.68 | 0.43 | diphenylphosphoric acid | 4.90 | acetonitrile | 4.0 | 50 | 30 min | 0 |
| 34 | 7-ACA 0.68 | 0.43 | dimethylphosphoric acid monomethylphosphoric acid | 4.06 2.70 | acetonitrile | 4.0 | 50 | 30 min | 0 |
| 35 | 7-ACA 1.36 | 0.87 | pyrophosphoric acid | 8.90 | acetic acid | 10.0 | 45–50 | 10 hr | 32.2 |
| 36 | 7-ABC 0.79 | 0.43 | phosphoric acid | 2.31 | acetonitrile | 3.8 | 50 | 1 hr | 0 |
| 37 | 7-ABC 1.57 | 0.87 | fuming sulfuric acid (SO$_3$ content: 30%) | 2.19 | acetonitrile | 7.5 | 50 | 1 hr | 0 |

What we claim is:

1. In the method for producing a 7-aminocephem compound of the formula:

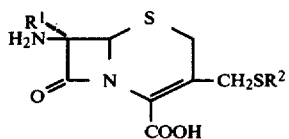

wherein $R^1$ is a hydrogen atom or methoxy group and $R^2$ is a residue of a thiol compound, or a salt or ester thereof which comprises reacting a compound of the formula:

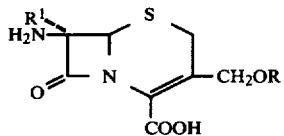

wherein $R^1$ is as defined above and R is a carboxylic acid acyl group, or a salt or ester thereof with a thiol compound or a salt thereof, wherein the improvement comprises conducting said reaction in an organic solvent in the presence of a dihalophosphoric acid.

2. An improved method as claimed in claim 1, wherein the dihalophosphoric acid is dichlorophosphoric acid.

3. An improved method as claimed in claim 1, wherein the dihalophosphoric acid is produced by reaction of diphosphoryl tetrahalide with water.

4. An improved method as claimed in claim 1, which comprises reacting a compound of the formula [I] or a salt or ester thereof, with a thiol compound or a salt thereof, water and diphosphoryl tetrachloride in an organic solvent.

5. An improved method as claimed in claim 3, wherein the diphosphoryl tetrahalide is diphosphoryl tetrachloride.

6. An improved method as claimed in claim 1 or 3, wherein used amount of the dihalophosphoric acid is 4 to 24 moles per 1 mole of the compound [I].

7. An improved method as claimed in claim 1 or 4, wherein the organic solvent is selected from a group consisting of nitriles, nitroalkanes, aromatic hydrocarbons, esters, halogenated hydrocarbons, organic carboxylic acids, ethers, sulfolanes and mixtures thereof.

8. An improved method as claimed in claim 1 or 4, wherein used amount of the organic solvent is 0.1 to 10.0 l per 1 mole of the compound [I].

9. An improved method as claimed in claim 1 or 4, wherein the carboxylic acid acyl group is acetoxy.

10. An improved method as claimed in claim 1 or 4, wherein the carboxylic acid acyl group is 3-oxobutyryl group.

11. An improved method as claimed in claim 1 or 4, wherein the residue of a thiol compound is a tetrazolyl group which may be substituted with $C_{1-4}$ alkyl, amino-$C_{1-4}$ alkyl, N-$C_{1-4}$ alkylamino-$C_{1-4}$alkyl or N,N-di-$C_{1-4}$alkylamino-$C_{1-4}$ alkyl.

12. An improved method as claimed in claim 11, wherein the tetrazolyl group is 1-(N,N-di-$C_{1-4}$ alkylamino-$C_{1-4}$ alkyl)-1H-tetrazolyl.

* * * * *